United States Patent
Bair, III et al.

(10) Patent No.: US 6,843,100 B2
(45) Date of Patent: Jan. 18, 2005

(54) THERMAL CONDUCTIVITY MEASUREMENT OF CARBON DIOXIDE GAS WITH RELATIVE HUMIDITY AND TEMPERATURE COMPENSATION

(75) Inventors: Richard H. Bair, III, Weaverville, NC (US); Charles G. Butts, Weaverville, NC (US); Bryan M. Elwood, Candler, NC (US)

(73) Assignee: Kendro Laboratory Products, L.P., Newtown, CT (US)

( * ) Notice: Subject to any disclaimer, the term of this patent is extended or adjusted under 35 U.S.C. 154(b) by 0 days.

(21) Appl. No.: 10/288,464

(22) Filed: Nov. 6, 2002

(65) Prior Publication Data

US 2003/0131653 A1 Jul. 17, 2003

Related U.S. Application Data

(60) Provisional application No. 60/347,237, filed on Jan. 14, 2002.

(51) Int. Cl.[7] .................................................. G01N 9/00
(52) U.S. Cl. ........................ 73/23.2; 73/23.21; 73/23.25
(58) Field of Search ................................ 73/23.2, 23.21, 73/23.25, 23.4; 435/3, 303.1, 300; 119/300

(56) References Cited

U.S. PATENT DOCUMENTS

| | | | | | |
|---|---|---|---|---|---|
| 3,929,584 | A | * | 12/1975 | Mansfield | 435/3 |
| 5,025,619 | A | * | 6/1991 | Cannon | 119/300 |
| 5,418,131 | A | * | 5/1995 | Butts | 435/3 |
| 5,540,077 | A | * | 7/1996 | Benning et al. | 73/1.05 |
| 5,897,836 | A | * | 4/1999 | Martell et al. | 422/90 |
| 6,010,243 | A | * | 1/2000 | Hessler et al. | 374/1 |
| 6,503,751 | B2 | * | 1/2003 | Hugh | 435/303.1 |

* cited by examiner

*Primary Examiner*—Hezron Williams
*Assistant Examiner*—Jacques M. Saint-Surin
(74) *Attorney, Agent, or Firm*—Baker & Hostetler LLP

(57) ABSTRACT

A carbon dioxide gas measurement and control system and method which comprises a thermal conductivity absolute humidity sensor which measures carbon dioxide during dynamic temperature and humidity changes by isolating the particular sensor response for absolute humidity and temperature, i.e., $Vm(D,T)$ in order to track carbon dioxide concentration.

13 Claims, 6 Drawing Sheets

RH, TEMP, CO2

THERMAL CONDUCTIVITY MEASUREMENT OF CARBON DIOXIDE GAS WITH RELATIVE HUMIDITY AND TEMPERATURE COMPENSATION

PRIORITY

This application claims priority to the provisional patent application 60/347,237 filed Jan. 14, 2002, the disclosure of which is incorporated herein by reference.

FIELD OF THE INVENTION

The present invention generally relates to a method and system for accurately measuring carbon dioxide gas concentration. More specifically, the present invention relates to measuring the thermal conductivity of carbon dioxide gas in a substantially saturated or non-saturated gaseous environment, e.g., a cell-culture incubator, and compensating for relative humidity and temperature variations.

BACKGROUND OF THE INVENTION

Measurement and control of carbon dioxide gas concentration in laboratory cell-culture incubators is most commonly accomplished by means of a thermal conductivity detection system. The thermal conductivity cell, or detector, is a differential thermometer, set up as an electronic bridge circuit that is balanced to be equal, with two thermistors in a common block or metallic housing to add thermal stability. (See U.S. Pat. No. 3,929,584 (Mansfield)). This cell is most commonly placed in a working environment that is isolated from the surrounding area, but is not restricted to its placement.

Moreover; U.S. Pat. No. 5,418,131 (Butts) shows a unique system for detecting or measuring $CO_2$ gas concentration in an enclosed environment using a thermal conductivity sensor.

In some instances, a detector cell is located in an air flow path external from the working environment, but contiguous with the environment. One thermistor sensor is enclosed in the block/housing and detects chamber temperature only. The other thermistor sensor is exposed to the chamber environment. The measured difference between the two thermistor sensors is the thermal conductivity (density) of the atmosphere, or its ability, when moved at an even rate, to remove the small amount of heat from the exposed sensor. If all other factors remain constant and only the carbon dioxide content is varied, the "TC" cell output (when properly calibrated) will indicate changes in carbon dioxide gas concentration. Unfortunately, the TC cell is affected by barometric pressure, temperature, humidity and the velocity of air flow past the sensor cell. These variables are controlled or compensated for with the use of electronic zeroing circuitry to compensate for changes in temperature and relative humidity levels. In monitoring the effects of carbon dioxide gas in an atmosphere, absolute humidity must be held constant so any change in thermal conductivity is caused only by a change in the carbon dioxide gas concentration. Under the worst circumstances, a change in absolute humidity can cause such a significant change in thermal conductivity that the controller can shift the carbon dioxide gas content by as much as 4%.

To maintain a stable humidity level in laboratory incubators, a pan of water is placed within the working environment and its temperature allowed to equilibrate. The incubator, working atmosphere, must reach a point of near saturation in order to maintain an absolute humidity level that will not change with ambient conditions.

For the laboratory investigator that does not want to operate their incubator in a saturated condition, but does want accurate carbon dioxide gas control, the drifting of the thermal conductivity sensor's reference becomes a problem with regard to the accuracy of the carbon dioxide gas concentration in the incubator. That is, as the absolute humidity changes, so does the reference base of the carbon dioxide gas sensor.

When operating a dry incubator, as opposed to a saturated one, ambient humidity fluctuations will effect carbon dioxide gas zero calibration. Since the fluctuations possible in extreme ambient temperature changes have less effect on the total absolute humidity, the carbon dioxide gas calibration can be affected as much as 1.5% in the worst case which does not represent as severe a problem, but does create an error that could prove critical in the pH level of the cell media being cultured within the incubator working chamber.

The two factors that contribute to inaccuracies in a thermal conductivity gas control system, i.e., relative humidity and dry-bulb temperature, are taken into consideration in the measurement system of the present invention to arrive at the absolute humidity and temperature compensated carbon dioxide gas concentration.

SUMMARY OF THE INVENTION

The present invention provides a method to compensate for humidity and temperature in a controlled environment.

The present invention also provides a method of quantifying an absolute humidity sensor for three dependent variables and isolating the desired variable e.g., $CO_2$.

The present invention includes a method of thermal conductivity measurement of $CO_2$ with relative humidity and temperature compensation as herein disclosed. In accordance with one embodiment of the present invention, this method ensures accurate readings without being sensitive to any specific hardware or sensors being utilized.

The present invention provides a humidity and temperature compensated carbon dioxide gas detection and control system in a controlled atmosphere environment, having a humidity sensor, a temperature sensor and a carbon dioxide adjustment control circuit.

Further, the present invention provides a method of humidity and temperature compensated carbon dioxide gas detection and control system in a controlled atmosphere environment, which includes sensing humidity level outputs, sensing thermal conductivity level outputs, comparing the humidity levels and the thermal conductivity levels to find carbon dioxide gas levels and adjusting the carbon dioxide gas levels.

The present invention provides a humidity and temperature compensated carbon dioxide gas detection and control system in a controlled atmosphere environment, having means for sensing humidity level outputs, means for sensing thermal conductivity level outputs, means for comparing the humidity levels and the thermal conductivity levels to find carbon dioxide gas levels and means for adjusting the carbon dioxide gas levels.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

The present invention provides a compensation method and system employing a quantification of the absolute humidity sensor 20 (e.g., the Mitsubishi HS-6 absolute humidity sensor) to measure the carbon dioxide response for each of the three dependent variables under consideration namely, absolute humidity (D), temperature (T) 32, and carbon dioxide gas 34 in an incubator or other controlled environment.

Figure 1:
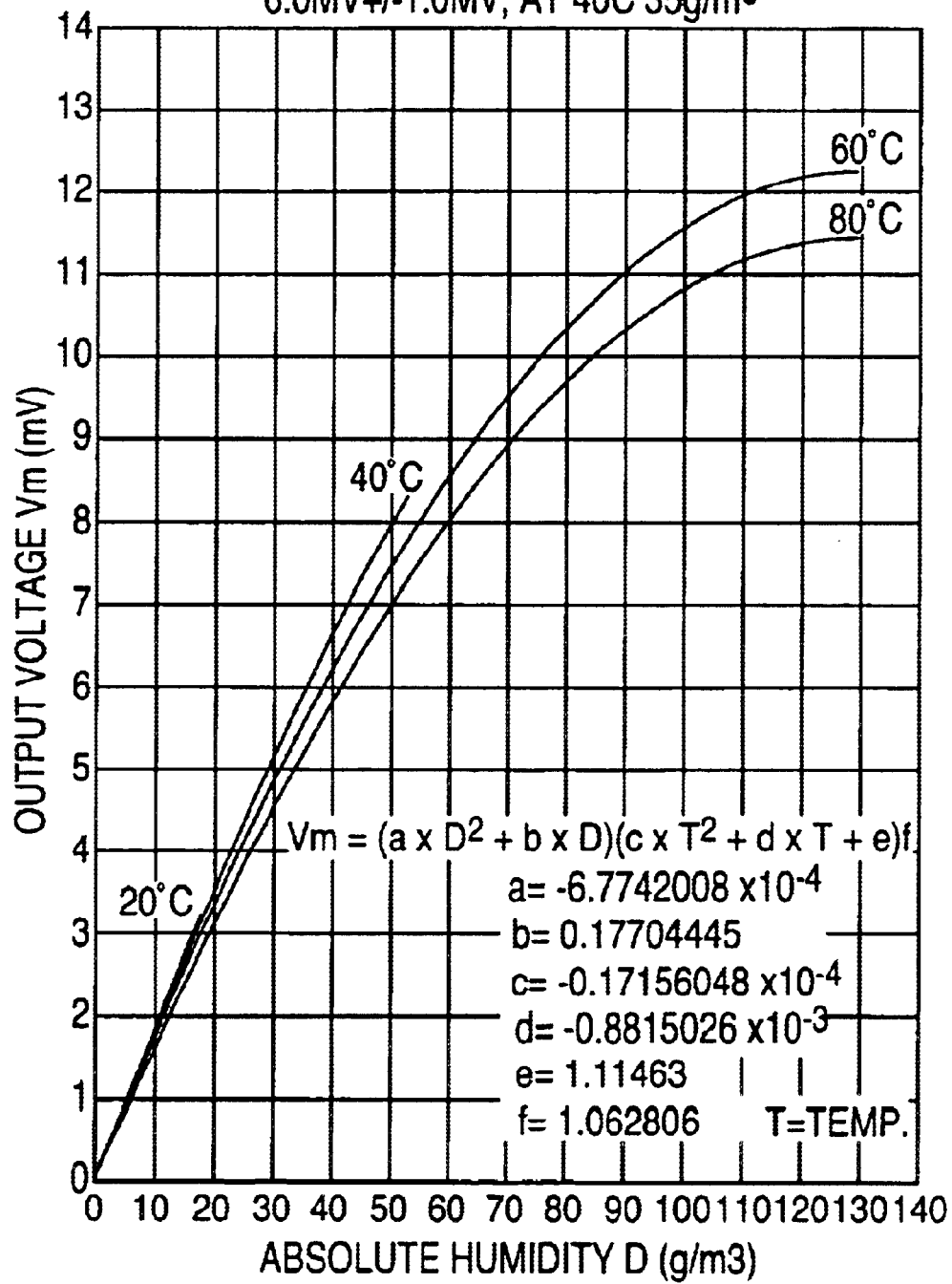
FIG. 1 is a graph depicting the output voltage of the absolute humidity sensor of one preferred embodiment of the present invention.

Referring to FIG. 1, the absolute humidity sensor response can be isolated with respect to the desired variable in order to read carbon dioxide gas. The absolute humidity sensor 20 to measure carbon dioxide has specifications that provide for a second order polynomial expression that describes the voltage response (Vm) as a function of absolute humidity (D) and temperature (T) in the following mathematical expression:

$$Vm(D,T)=(aD^2+bD)(cT^2+dT+e)f$$

with, a=−6.7742008E4
b=0.17704445
c=−0.17156048E4
d=−0.88115026E-3
e=1.11463
f=1.062806

Figure 4:
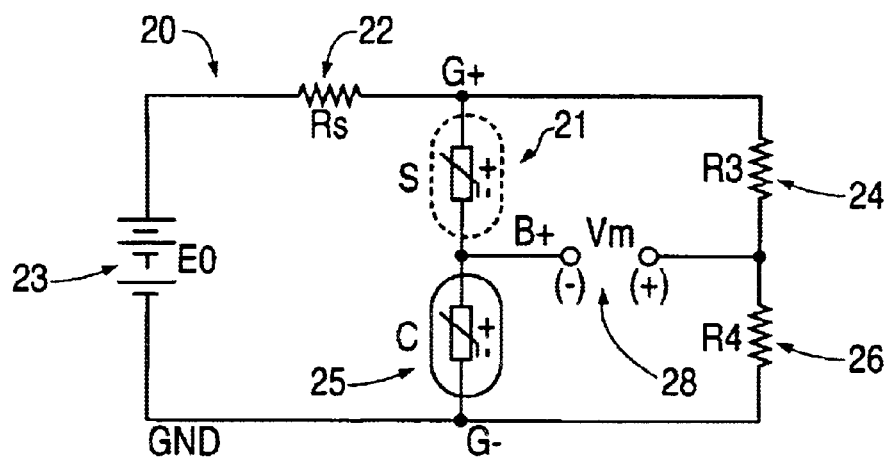
FIG. 4 shows an inspection circuit for measuring $Vm(D,T)$ of one preferred embodiment of the present invention.

It provides voltage as a function of absolute humidity and temperature, i.e., $Vm(D,T)$ using the circuit shown in FIG. 4.

Thus if D and T are known, then $Vm(D, T)$ can be obtained, i.e. the voltage response of the absolute humidity sensor for measuring carbon dioxide to absolute humidity and temperature.

Figure 2:
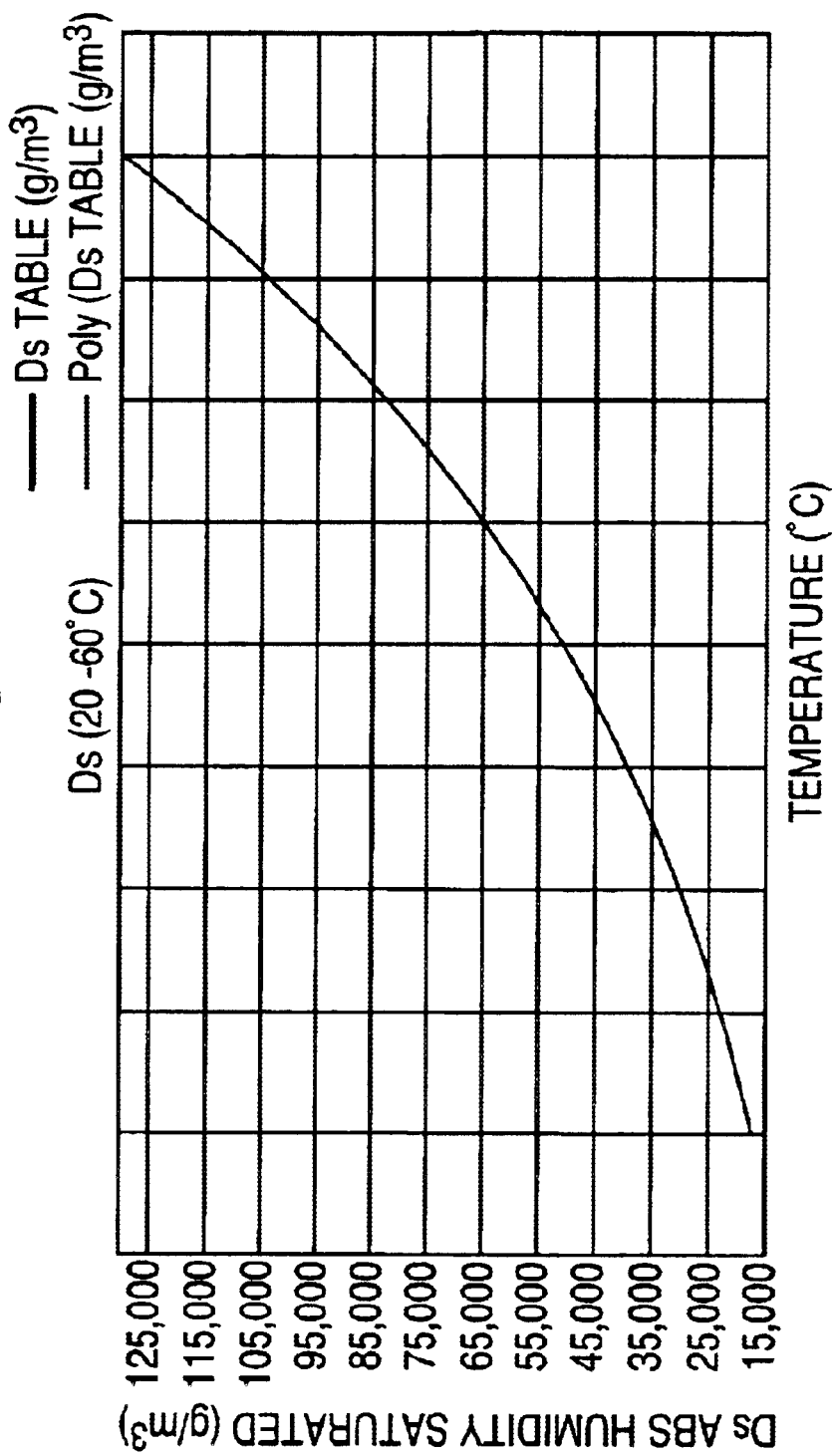
FIG. 2 is a graph depicting the absolute humidity calculation over the range of temperature operation for one preferred embodiment of the present invention.
Figure 3:
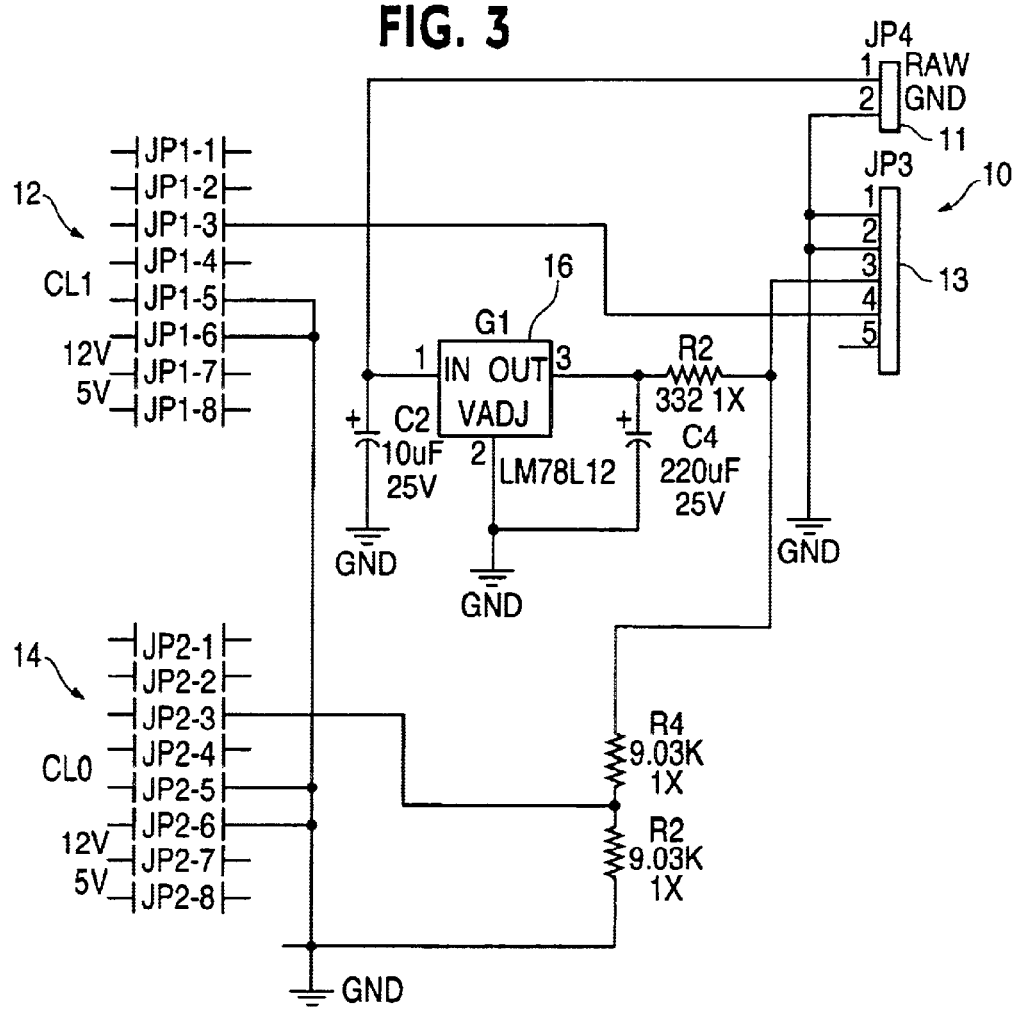
FIG. 3 is a schematic depicting the absolute humidity sensor circuitry of one preferred embodiment of the present invention.

Referring to FIGS. 2–4, temperature (T) is obtained directly via the cabinet RTD sensor 21 (makes temperature measurements and ignores any offset to the center of the enclosure or incubator). Absolute humidity (D) can be calculated using numerous techniques, this embodiment uses a relative humidity sensor that is temperature compensated first and then converted to absolute humidity using the following fourth order polynomial which is designed for accuracy in the 20 to 60° C. temperature range:

$$D(T)=4E\text{-}06T^4+2E\text{-}05T^3+0.0158T+0.2313T+5.5676$$

Again, referring to FIGS. 3 and 4, the voltage response (Vm) 28 of the absolute humidity sensor 20 that measures carbon dioxide due to absolute humidity and temperature can be readily solved for by using the RTD sensor 21 and temperature compensation element 25 of the relative humidity sensor inputs. Once $Vm(D,T)$ is solved, then the absolute humidity sensor voltage response is quantified for two of the three variables. Thus, any measured deviation from $Vm(D, T)$ is therefore due to carbon dioxide gas. The temperature coefficient for resistor 22 is preferred to be 50 $\Omega/°$ C. or under and the temperature coefficient of resistor 24 is preferred to be 5 $\Omega/°$ C. or under. Resistor 26 is a variable resistor type and voltage 23 is preferred to be 16V±0.1VDC. In addition, each absolute humidity sensor 20 measures carbon dioxide using corresponding circuitry 10 which includes sensor connectors 11, 13, a regulator 16 and controller connectors 12, 14 can be zeroed with the firmware. It should be noted that other gases such as oxygen can also have an effect on thermal conductivity measurements and can be compensated for.

Figure 5:
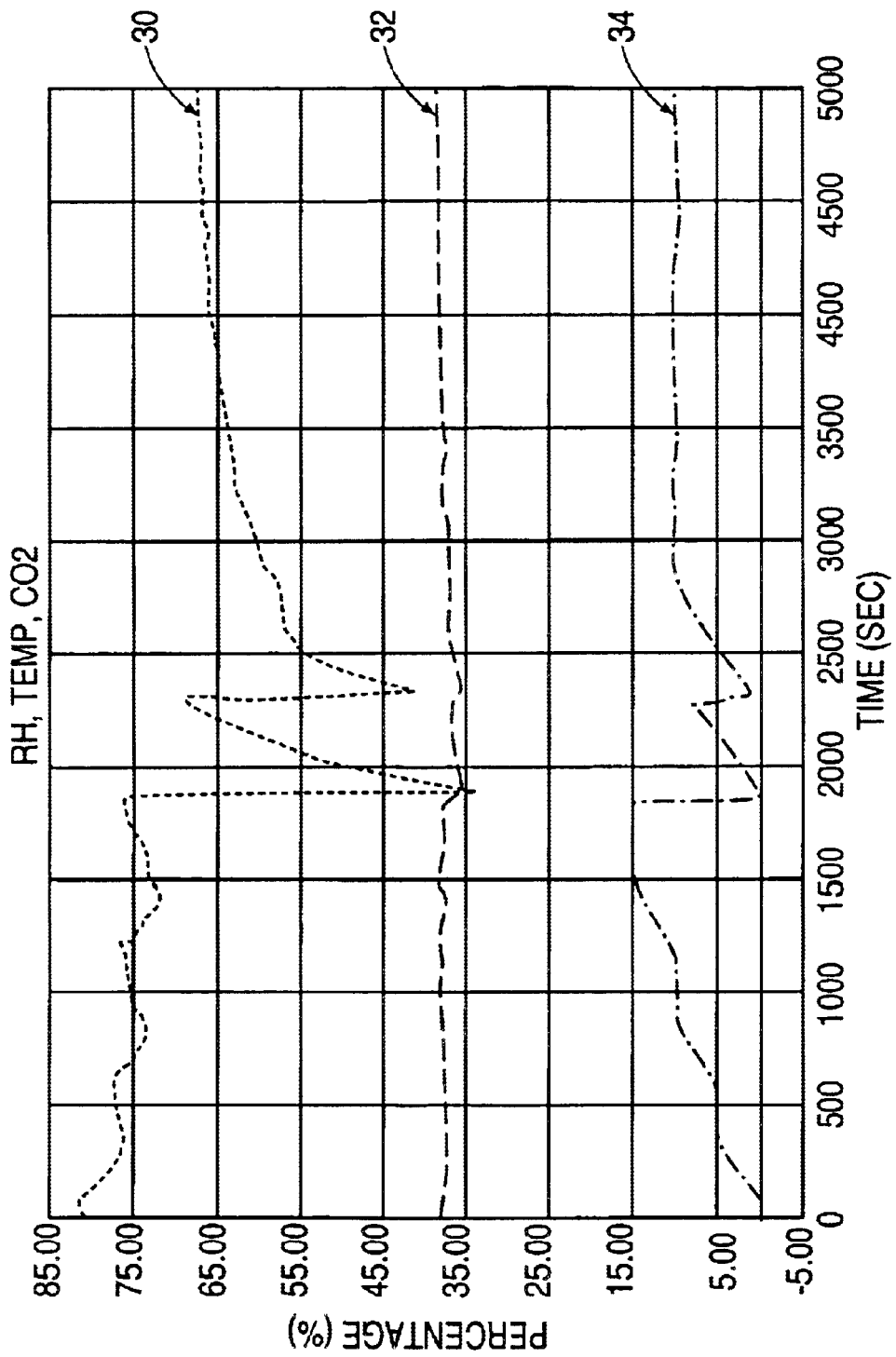
FIG. 5 shows the relative humidity, carbon dioxide and temperature relationships with compensation and different carbon dioxide setpoints of one preferred embodiment of the present invention.

Referring to FIG. 5, the absolute humidity sensor 20 to measure carbon dioxide 34 has a voltage response that is reduced by increases in carbon dioxide concentration in a linear fashion and yields carbon dioxide percent ([$Vm(D, T)$-$V_{actual}$]/$CO_2$ span, thus yielding $CO_2$ concentration). Each absolute humidity sensor 20 can have varied sensitivity to carbon dioxide gas and therefore the firmware allows the user to set the sensitivity in micro-volts per percent carbon dioxide gas, ie., $CO_2$ span. It should be noted that this method is not sensitive to any specific hardware except for the absolute humidity sensor 20 to measure carbon dioxide, it merely requires independent measurement of absolute humidity (D) and temperature (T) 32. Therefore, if sensors, other than those employed in the preferred embodiment are selected, it is a trivial matter to adjust and utilize the above method. It should also be noted when relative humidity 30 is controlled, this compensation scheme is still effective. In addition, other sensors like the HS-6 absolute humidity sensor could be quantified in their response to absolute humidity and temperature to dynamically compensate and effectively track $CO_2$ concentration.

Figure 6:
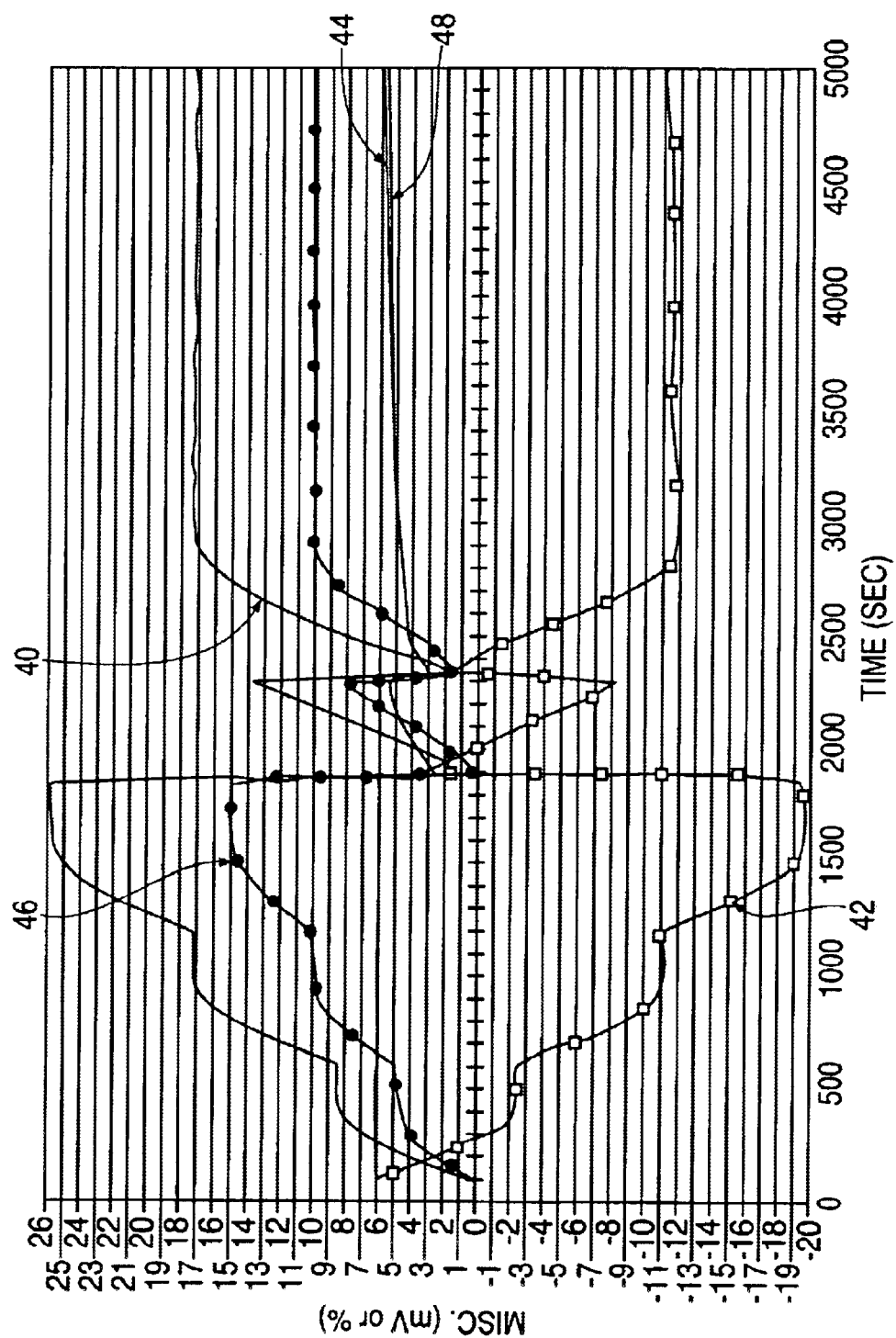
FIG. 6 shows the actual verses calculated absolute humidity sensor (HS-6) response to compensation over time of one preferred embodiment of the present invention.

Referring to FIG. 6, the graphic shows that the voltage response (Vm) 40, 44 of the HS-6 absolute humidity sensor remains stable and linear with respect to its carbon dioxide response for estimated percent $CO_2$ error 46 and relative humidity with 3 percent correction 48 as the temperature and humidity change verses the actual response 42.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A humidity and temperature compensated carbon dioxide pas detection and control system in a controlled atmosphere environment, comprising:
   means for sensing humidity level outputs;
   means for sensing thermal conductivity level outputs;
   means for comparing said humidity levels and said thermal conductivity levels to find carbon dioxide gas levels; and
   means for adjusting said carbon dioxide gas levels, wherein the means for sensing thermal conductivity level outputs is a RTD sensor and wherein the means for comparing said humidity level outputs and said thermal conductivity level outputs is the following formula:

$$D(T)=4E\text{-}06T^4+2E\text{-}05T^3+0.0158T^2+0.2313T+5.5676,$$

where D is the absolute humidity level and T is temperature as measured by said RTD sensor.

2. The system of claim 1, wherein the means for sensing humidity level outputs is a relative humidity sensor.

3. The system of claim 1, wherein the means for adjusting the carbon dioxide levels comprises a voltage response of an absolute humidity sensor for measuring carbon dioxide to absolute humidity and temperature determined by the formula: $Vm(D,T)=(aD^2+bD)(cT^2+dT+e)f$ with, $a=-6.7742008E\text{-}4$, $b=0.17704445$, $c=-0.17156048E\text{-}4$, $d=-0.88115026E\text{-}3$, $e=1.11463$, and $f=1.062806$.

4. A method of humidity and temperature compensated carbon dioxide gas detection and control system in a controlled atmosphere environment, comprising the steps of:
   sensing humidity level outputs;
   sensing thermal conductivity level outputs;
   comparing said humidity levels and said thermal conductivity levels to find carbon dioxide gas levels; and
   adjusting said carbon dioxide pas levels, wherein the thermal conductivity level outputs utilize a RTD sensor and wherein the humidity levels and said thermal conductivity levels comparison utilize the following formula:

$$D(T)=4E\text{-}06T^4+2E\text{-}05T^3+0.0158T^2+0.2313T+5.5676,$$

where D is the absolute humidity level and T is temperature as measure by said RTD sensor.

5. The method of claim 4, wherein humidity level outputs utilize a relative humidity sensor.

6. The method of claim 4, wherein the carbon dioxide levels are adjusted via a voltage response of an absolute humidity sensor for measuring carbon dioxide to absolute humidity and temperature determined by the formula: $Vm(D,T)=(aD^2+bD)(cT^2+dT+e)f$ with, $a=-6.7742008E4$, $b=017704445$, $c=-0.17156048E\text{-}4$, $d=-0.88115026E\text{-}3$, $e=1.11463$, and $f=1.062806$.

7. A humidity and temperature compensated carbon dioxide gas detection and control system in a controlled atmosphere environment, comprising:
   a humidity sensor;
   a temperature sensor; and
   a carbon dioxide adjustment control circuit, wherein the carbon dioxide adjustment control circuit further comprises:
   a first thermistor connected in series to a second thermistor;
   at least one variable resistor;
   a voltage source; and
   a voltage output, wherein said temperature sensor is a RTD sensor and wherein the voltage output determines the deviation due to carbon dioxide gas based on the formula:

$$Vm(D,T)=(aD^2+bD)(cT^2+dT+e)f \text{ with, } a=-6.7742008E\text{-}4,$$
$$b=0.17704445, c=-0.17156048E\text{-}4, d=-0.88115026E\text{-}3,$$
$$e=1.11463, \text{ and } f=1.062806$$

where D is absolute humidity and T is temperature as measured by said RTD sensor.

8. The system of claim 7, wherein said humidity sensor is a relative humidity sensor.

9. The system of claim 7, wherein said voltage source is a DC voltage.

10. The system of claim 7, wherein said first thermistor has a temperature coefficient of 50 $\Omega$/° C. or less.

11. The system of claim 7, wherein said second thermistor has a temperature coefficient of 5 $\Omega$/° C. or less.

12. The system of claim 7, wherein said absolute humidity is determined by the formula: $D(T)=4E\text{-}06T^4+2E\text{-}05T^3+0.0158T^{2+0.2313}T+5.5676$, where T is temperature as measured by said RTD sensor.

13. The system of claim 7, wherein said temperature sensor and said humidity sensor are connected in parallel to said voltage source.

* * * * *

UNITED STATES PATENT AND TRADEMARK OFFICE
CERTIFICATE OF CORRECTION

PATENT NO.    : 6,843,100 B2
DATED         : January 18, 2005
INVENTOR(S)   : Richard H. Bair, III et al.

It is certified that error appears in the above-identified patent and that said Letters Patent is hereby corrected as shown below:

<u>Column 6,</u>
Line 46, pleae replace "$0.0158T^{2+0.2313}T$" with -- $0.0158T^2+0.2313T$ --

Signed and Sealed this

Fifth Day of April, 2005

JON W. DUDAS
*Director of the United States Patent and Trademark Office*